United States Patent [19]

Burke

[11] Patent Number: 4,909,965
[45] Date of Patent: Mar. 20, 1990

[54] SALCOMINE-CATALYZED OXIDATION OF PHENOLS

[75] Inventor: Patrick M. Burke, Wilmington, Del.

[73] Assignee: E. I. Du Pont de Nemours and Company, Wilmington, Del.

[21] Appl. No.: 289,710

[22] Filed: Aug. 3, 1981

[51] Int. Cl.$^4$ .............................................. C07C 46/08
[52] U.S. Cl. ..................................................... 552/309
[58] Field of Search ..................................... 260/396 R

[56] References Cited

U.S. PATENT DOCUMENTS

| 3,658,852 | 4/1972 | Schuster et al. | 260/396 R |
| 3,859,317 | 1/1975 | Hutchings | 260/396 R |
| 3,966,776 | 6/1976 | Kato et al. | 260/396 R |
| 3,987,068 | 10/1976 | Reilly | 260/396 R |

OTHER PUBLICATIONS

Fullerton et al, Tetrahedron Letters, No. 2, pp. 139–142, 1976.

Van Dort, H. M., et al., Rec. Trav. Chim. 86, 520–526 (1967).

Vogt, L. H., Jr., et al., Journal of Organic Chemistry 34, 273–277 (1969).

Kothari, V. M., et al., Journal of Catalysis 41, 180–189 (1976).

*Primary Examiner*—Vivian Garner

[57] ABSTRACT

The life of a salcomine catalyst used in the oxidation of phenols to quinones (e.g., of o-phenylphenol to phenyl-p-benzoquinone) is increased by the presence of a water- or acid-removing substance, e.g., a non-acid-forming chemical water scavenger, a molecular sieve, a weak inorganic base, or a sterically hindered organic base, in the reaction medium. Suitable water- or acid-removing substances include carbodiimides, e.g., dicyclohexylcarbodiimide; a Type 3A or 4A molecular sieve; finely divided metal oxides or metal carbonates, e.g., barium carbonate; and 2,6-lutidine. These substances chemically transform by-product carboxylic acids, and/or prevent the formation of such acids, whereby the life of the salcomine catalyst is prolonged.

10 Claims, No Drawings

SALCOMINE-CATALYZED OXIDATION OF PHENOLS

BACKGROUND OF THE INVENTION

1. Field of the Invention

The present invention relates to the oxidation of substituted phenols to form quinones, and more particularly to the oxidation of such compounds by means of an oxygen-containing gas in the presence of a salcomine catalyst.

2. Description of the Prior Art

The synthesis of quinone, e.g., benzo- and diphenoquinones, by the catalytic oxidation of phenols in the liquid phase has been widely reported. Catalysts which have been found useful in this synthesis include soluble copper-nitrile complexes (U.S. Pat. No. 3,987,068) and salcomines (Van Dort, H. M., et al., Rec. trav. chim. 86, 520–526 (1967); Vogt, L. H., Jr., et. al., J. Org. Chem. 34, 273–277 (1969); Kothari, V. M., et al., J. Catalysis 41, 180–189 (1976); U.S. Pat. Nos. 3,859,317 and 3,966,776).

While the salcomine-catalyzed oxidation is attractive for the synthesis of certain 1,4-quinones because it affords high selectivity for the desired product and presents fewer corrosion problems than are encountered in other catalyst systems, the process as heretofore practiced has attracted little commercial interest because of the relatively small amount of quinone produced per mole of catalyst. In the past, the salcomine catalyst became totally, and apparently irreversibly, inactive after a number of oxidation cycles which was too small to overcome its relatively high price.

SUMMARY OF THE INVENTION

The present invention provides an improvement in a method of oxidizing a substituted phenol having a free para position with an oxygen-containing gas in an inert organic solvent in the presence of a salcomine catalyst to produce a quinone and water, which improvement comprises carrying out the oxidation in the presence of an agent which chemically transforms, e.g., neutralizes or dehydrates, by-product carboxylic acids, and/or which prevents the formation of such acids, in the reaction mixture, whereby the life of the salcomine catalyst is prolonged. The reaction mixture contains an inert organic solvent for the phenol, the catalyst, any phenol that may still be unreacted, and, as the oxidation reaction proceeds, the oxidation product(s). The catalyst-life-prolonging agent may be added to this mixture as the oxidation proceeds, but preferably is added to the catalyst-containing phenol solution before the oxidation begins.

The preferred agents for chemically transforming the carboxylic acid(s), or preventing the formation thereof, in the reaction mixture are non-acid-forming chemical water scavengers, most preferably carbodiimides; molecular sieves, e.g., Types 3A and 4A molecular sieves; and weak bases, most preferably finely divided metal oxides or carbonates or sterically hindered organic bases such as 2,6-lutidine.

DETAILED DESCRIPTION

The present invention is based on the finding that the presence of a chemical water scavenger such as dicyclohexylcarbodiimide (DCCI), or a molecular sieve, in the reaction mixture in which a substituted phenol is undergoing salcomine-catalyzed oxidation significantly extends the life of the catalyst, i.e., increases the number of moles of quinone obtained per mole of salcomine. For example, in the oxidation of an aryl-substituted phenol, o-phenylphenol, to a 1,4-quinone, phenyl-p-benzoquinone, the total number of oxidation cycles or turnovers obtained with the present process (one cycle or turnover being equal to the production of one mole of the 1,4-quinone per mole of catalyst added) normally is in the range of about from 50 to 100, whereas it is only in the range of about from 20 to 30 cycles when the described water-removers are absent. An extension of catalyst life of this magnitude is of considerable importance especially in the case of salcomine catalysts, which are relatively expensive products when compared to the simple salts which have been used in the past for phenol oxidations.

It has been found that exposure of salcomine catalysts to carboxylic acids results in an apparently irreversible catalyst-deactivating reaction. While I do not intend that my invention be limited in any way by theoretical considerations, I have obtained evidence that dicarboxylic acids are produced during phenol oxidations, and this may occur by a reaction of an oxidation by-product, an o-quinone for example, with water, one mole of which forms as an oxidation by-product per mole of quinone formed. It is my belief that the increased catalyst life observed when DCCI is present is due to the fact that the removal of water prevents the formation of carboxylic acids and/or transforms carboxylic acids into anhydrides. The importance of eliminating carboxylic acids from the reaction medium is substantiated by the finding that the desired catalyst-protecting effect is also achieved if an appropriate weak base is added to transform any carboxylic acids present into salts.

In the present process, the compound which undergoes oxidation to a quinone is a monohydroxy-substituted aryl compound which is substituted in one or more of the positions ortho or meta to the hydroxyl group and unsubstituted in the position para to the hydroxyl group. Single- as well as multiple-ring aryl compounds, preferably mono- and bicyclic compounds, can be used. Suitable substituents include aryl, alkyl, aralkyl, and alkoxy groups. Benzene rings in aryl or aralkyl substituents may be unsubstituted, or they may in turn contain non-halo substituents, e.g., alkyl and alkoxy substituents. Alkyl substituents preferably have 1 to 4 carbon atoms. A preferred phenol is o-phenylphenol, which is oxidized to phenyl-p-benzoquinone, a useful intermediate for polymers.

The oxidation is carried out in the liquid phase, i.e., while the phenol is in solution in an organic solvent. Any organic liquid which is inert and capable of dissolving the phenol at the reaction temperature employed is suitable as a solvent. "Inert" means that the solvent is not itself oxidizable under the reaction conditions employed, and is not so strongly acidic or basic as to deactivate the salcomine catalyst. While polar solvents such as dimethylformamide (DMF), N-methylpyrrolidone, and methanol, as well as nonpolar solvents such as benzene and toluene may be used, the weakly basic polar solvents such as acetonitrile, benzonitrile, and DMF, which are capable of forming weak adducts with the salcomine, are preferred.

The term "salcomine" as used herein denotes a bis(salicylaldiminato) cobalt(II) complex capable of reacting reversibly with molecular oxygen and having the following structure:

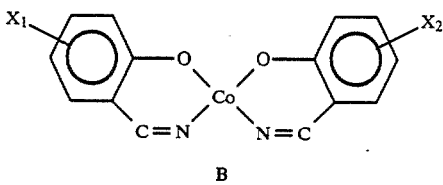

B wherein $X_1$ and $X_2$ are H, alkyl, aryl, alkoxy, halo, or nitro, and B is a bridging group selected from bivalent 2- or 3-carbon atom alkylene radicals, i.e., the ethylene (—CH$_2$—CH$_2$—) or 1,3-propylene (—CH$_2$—CH$_2$—CH$_2$—) radical, which can be unsubstituted or 1-3 carbon alkyl-substituted, e.g., the 1,2-propylene

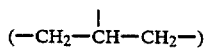

or 2-methyl-1,2-propylene

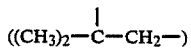

radical; and pairs of adjacent carbon atoms in a saturated cycloaliphatic radical, e.g., the 1,2-cyclohexylene radical, or in an aromatic radical, e.g., the o-phenylene radical. B also may be a 3-aza-1,5-pentylene or 4-aza-1,7-heptylene radical of the formula

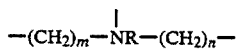

wherein m and n are 2 or 3 and R is a 1-3 carbon alkyl group or H. The nitrogen in this chain bonds with the cobalt.

The salcomine catalyst is a Schiff base coordination compound of salicylaldehyde, cobalt, and a diamine from which the above radicals are derived. These compounds include, for example, bis(salicylidene)ethylenediimino cobalt(II), bis(salicylidene)-o-phenylenediimino cobalt(II), bis(salicylidene)propylene-1,2-diimino cobalt(II), bis(salicylidene)-2-methyl-1,2-diiminopropane cobalt(II), bis(salicylidene)-1,2-diiminocyclohexane cobalt(II), bis(3-methoxysalicylidene)ethylenediimino cobalt(II), bis(5-chloro- and bis(5-bromosalicylidene)ethylenediimino cobalt(II), and cobalt(II) bis(salicylidene-γ-iminopropyl)methylamine. In the latter, B is

and the nitrogen is bonded to the cobalt. Catalysts of this type have been described as homogeneous for the oxidation of phenols in organic media inasmuch as they generally dissolve, at least partially, as the oxidation progresses.

Thus, in the oxidation reaction mixture the salcomine catalyst is present in at least a partially dissolved state. Also present in the reaction mixture is a water- or acid-removing substance which either (a) reacts with or absorbs water so as to prevent the formation of carboxylic acids, by the reaction of water with a by-product, o-quinone, for example; or (b) chemically transforms any carboxylic acids present, e.g., reacts to form an anhydride or metal or amine salt of a carboxylic acid. Preferred catalyst-protective additives are the non-acid-forming chemical water scavengers, i.e., water scavengers which do not form acids on reacting with water. Such scavengers include acetals, ketals, ortho-formates, vinyl ethers, and the dialkyl, dicycloalkyl, and diaryl carbodiimides. Particularly preferred is the homogeneous water scavenger, dicyclohexylcarbodiimide (DCCI). The carbodiimide may react with the by-product water to form a urea; or, if a carboxylic acid has formed, the carbodiimide may convert the acid to its anhydride, a urea being formed by this route also. The formation of dicyclohexylurea in DCCI-controlled phenol oxidation reactions has been confirmed by infrared analysis.

Molecular sieves, which, as heterogeneous water scavengers, remove the by-product water by physical adsorption, also are effective in extending the life of the salcomine catalyst. Type 3A and 4A sieves, which are capable of adsorbing molecules having critical diameters up to 3 and 4 angstroms, respectively, can be used, the specific choice in any case being dependent on the organic solvent employed. With solvents such as acetonitrile and methanol, Type 3A sieves are more efficient and therefore preferred. Type 4A sieves are preferred with solvents such as DMF.

Physical adsorbents such as magnesium sulfate and sodium sulfate do not extend catalyst life, however.

A weak base, added to the reaction medium as an acid-removing substance, also extends catalyst life. The term "weak base" denotes herein a base which is not strong enough to displace cobalt from the salcomine catalyst and is incapable of blocking oxygen adduct formation by coordinating strongly with the cobalt. Metal oxides or carbonates, e.g., barium oxide or carbonate, preferably added as a fine dispersion may be used, as well as sterically hindered organic bases, e.g., 2,6-lutidine. These are bases whose nitrogen atom, while capable of protonating readily, is so sterically crowded as to be unable to coordinate with free coordination sites on the cobalt atom of the catalyst.

The solution of the substituted phenol containing the salcomine catalyst and the water- or acid-removing substance is contacted with an oxygen-containing gas, e.g., oxygen itself, air, or another mixture of oxygen diluted with an inert gas, under an oxygen partial pressure of at least 100, preferably at least about 300, kilopascals. Oxygen partial pressures as high as about 8000 kilopascals can be used. Temperatures can range from about 25° C. to about 10° C., a preferred range being about from 40° to 60° C. The specific temperature and oxygen pressure used will be selected on the basis of the phenol being oxidized, the desired quinone, and the desired oxidation rate. In the preparation of phenyl-p-benzoquinone from o-phenylphenol, for example, larger amounts of the phenol are consumed as the temperature is increased to above about 100° C., but by-product formation is extensive. Below about 25° C., this oxidation proceeds very slowly.

The amount of water- or acid-removing substance required in the present process can be determined for a given agent in the following manner: In the reaction, one mole of water is formed per mole of phenol oxidized. Therefore, one can calculate the amount of water produced from the amount of phenol used at the operating level of conversion, and determine the amount of a chemical water scavenger required to react with all of the water. One mole of DCCI, acetal, ketal, ortho-formate, or vinyl ether is required per mole of water. The required amount of a molecular sieve can be determined from the capacity of the sieve. When a weak base is used to neutralize a carboxylic acid, the amount of base required may be estimated by assuming that a dicarboxylic acid, e.g., a dihydromuconic acid, is formed by the hydrolysis of a by-product o-benzoquinone on a 1/1 molar basis. This o-quinone typically is 5–10% of the oxidation product, and therefore the amount of weak base employed must be sufficient to neutralize all of the dicarboxylic acid which could form by hydrolysis of the amount of o-quinone estimated to be formed.

The method of the invention will now be described by means of the following illustrative examples:

EXAMPLES 1–3

A 10-cc stainless steel shaker tube was charged with 5 millimeters of a solution of 1.7 grams of o-phenylphenol in acetonitrile; 2 milliliters of acetonitrile; 0.5 gram of dicyclohexylcarbodiimide ($C_6H_{11}N=C=NC_6H_{11}$); and 18 milligrams of bis(salicyclidene)-o-phenylenediimino cobalt(II). The acetonitrile solution also contained 0.5 gram of phenanthrene, which was an internal standard for gas chromatographic analysis. The tube was heated to 50° C. with agitation and pressurized with oxygen to a total pressure of 3447 kPa. After two hours at 50° C., during which time oxygen was added to maintain the pressure at 3447 kPa, the tube was cooled in dry ice and vented, and the tube contents were washed out with acetonitrile and made up to a standard volume of 50 ml therewith. This solution was analyzed for o-phenylphenol (OPP) and phenyl-p-benzoquinone (PBQ) by reversed-phase liquid chromatography. The procedure was repeated three times, twice with different amounts of the diimide (DCCI), and once with no diimide. Analysis of the acetonitrile solutions obtained in the four experiments gave the results summarized in the following table:

| Example No. | 1 | 2 | 3 | Control |
|---|---|---|---|---|
| grams DCCI | 0.5 | 1.0 | 2.0 | 0 |
| OPP concn. (g/l) | 15.0 | 8.8 | 1.9 | 29.0 |
| PBQ concn. (g/l) | 9.6 | 12.7 | 14.9 | 4.6 |
| (a)% OPP converted to PBQ | 26.0 | 34.5 | 40.7 | 12.5 |
| (b)No. of catalyst turnovers | 52.5 | 69.1 | 81.5 | 25.0 |

(a)[wt. PBQ formed/wt. OPP charged × 1.09] × 100; 1.09 = PBQ mol. wt./OPP mol. wt.
(b)moles PBQ formed per mole of catalyst added The above table shows that the presence of DCCI resulted in a large increase in the amount of OPP converted to PBQ and in the catalyst life. Moreover, higher conversions and more catalyst turnovers (cycles) were obtained as the amount of DCCI was increased from 0.24 mole (Example 1) to 0.96 mole (Example 3) per mole OPP.

EXAMPLE 4

The procedure described for carrying out Example 3 was repeated except that twice the amount of catalyst was used, i.e., 1 mole-% with respect to OPP as contrasted to b 0.5 mole-% in Example 3. The percent OPP converted to PBQ was 47.6. However, with the higher catalyst concentration, the number of catalyst turnovers dropped to 47.7, still nearly twice the turnovers achieved with the control.

EXAMPLE 5

The procedure of Example 1 was repeated with the exception that the dicyclohexylcarbodiimide was replaced by 2.09 grams of Linde Molecular Sieve Type 3A, an alkali metal alumino-silicate capable of absorbing molecules having critical diameters up to 3 angstroms. The molecular sieve had been conditioned by heating at 400° C. for 4 hours. In this case the catalyst had been modified by pre-treatment with oxygen in methylene chloride. The OPP concentration of the acetonitrile solution was 22.1 g/l; the PBQ concentration was 8.8 g/l. The percent OPP converted to PBQ was 23.9, and the number of catalyst turnovers 47.9. When the molecular sieve was omitted, the OPP concentration was 28.5 g/l and the PBQ 5.5 g/l. The percent OPP converted to PBQ was 14.9, and the number of catalyst turnovers 30.0.

CONTROL EXPERIMENTS

Although the chemical water scavenger, dicyclohexylcarbodiimide, and the Type 3A molecular sieve increased the conversion of o-phenylphenol to phenyl-p-benzoquinone, physical absorbents such as magnesium and sodium sulfates did not significantly improve catalyst life, as is shown by the following experiments:

The procedure of Example 1 was repeated except that the DCCI was omitted, and the amount of catalyst was increased to 76 mg, i.e., 2 mole-% with respect to OPP. In addition, 0.5 g of anhydrous magnesium sulfate was added to the reaction liquid in Experiment A, and 0.5 g of anhydrous sodium sulfate in Experiment B. The results are summarized in the following table:

| Expt. No. | A | B | C |
|---|---|---|---|
| % OPP converted to PBQ | 35.6 | 33.7 | 31.0 |
| No. of catalyst turnovers | 17.8 | 16.9 | 15.5 |

EXAMPLE 6

The procedure of Example 1 was repeated except that the dicyclohexylcarbodiimide was replaced by 0.25 milliliter of Lubrizol ®-565, a dispersion of 33% barium carbonate in mineral oil, manufactured by the Lubrizol Corporation. The OPP concentration of the acetonitrile solution was 26.9 g/l; the PBQ concentration was 6.1 g/l. The precent OPP converted to PBQ was 16.6, and the number of catalyst turnovers 33.2.

EXAMPLE 7

A 10-cc Hastelloy C shaker tube was charged with 2.5 milliliters of acetonitrile, 2.5 milliliters of 2,6-lutidine, 1.22 grams of 2,6-dimethylphenol, 9.3 milligrams of bis(salicylidene)-o-phenylenediimino cobalt(II), and 0.5 grams of phenanthrene (internal standard). The tube was heated with agitation to 50° C. at 690 kPa oxygen pressure. The reaction was terminated when further pressure drop became negligible, i.e., after about 3.5 hours. Oxygen was added throughout to maintain the pressure at 690 kPa. The tube was cooled to room temperature and vented, and the tube contents washed out with acetonitrile and made up to a standard volume of 50 ml therewith. Two control experiments, A and B, also were carried out. In one (A), the 2,6-lutidine was replaced by 2.5 milliliters of acetonitrile. In the other (B), the 2,6-lutidine was replaced by 2.5 milliliters of pyridine. The results were as follows:

|  | Ex. 7 | Control Expt. A | Control Expt. B |
|---|---|---|---|
| % phenol converted to 2,6-dimethyl-p-benzoquinone | 19.5 | 12.9 | 3.3 |
| No. of catalyst turnovers | 88 | 51.5 | 13 |

These results show that 2,6-lutidine, a non-coordinating organic base for the salcomine catalyst, produces a substantial increase in catalyst life. In contrast, pyridine, a coordinating base for the catalyst, reduced catalyst life.

EXAMPLE 8

The procedure described in Example 7 was repeated except that the amount of acetonitrile used was 5 milliliters, the lutidine was replaced by 1.03 grams of DCCI, the salcomine catalyst concentration was increased to 18.6 milligrams, and the oxygen pressure was increased to 1380 kPa. Analysis showed that 70.5% of the dimethylphenyl had been converted to products, with a 69.8% yield of 2,6-dimethyl-p-benzoquinone (percent conversion to this quinone divided by percent phenol consumed × 100). The number of catalyst turnovers, in terms of moles of the quinone produced per mole of catalyst added, was 98.5.

When the procedure was repeated but with the omission of the DCCI, only 25.0% of the phenol was consumed. The yield of 2,6-dimethyl-p-benzoquinone was 53.2%, and there were only 50 catalyst turnovers.

EXAMPLE 9

The procedure of Example 1 was repeated with the exception that the 2 milliliters of acetonitrile was replaced by 2 milliliters of triethyl orthoformate and the diimide was omitted. As in Example 5, the catalyst had been modified by pre-treatment with oxygen in methylene chloride. The OPP concentration in the diluted product solution was 27.4 g/l, and the PBQ concentration was 8.3 g/l. The percent OPP converted was 19.4, and the number of catalyst turnovers was 45.2.

EXAMPLE 10

The procedure described in Example 9 was repeated except that the ortho-formate was replaced by 1.4 grams of 1-cyclohexenylethyl ether. In the product solution the OPP concentration was 25.9 g/l and the PBQ concentration 7.5 g/l. The percent OPP converted was 23.8, and the number of catalyst turnovers was 40.7.

I claim:

1. In a method of oxidizing a substituted phenol having a free para position with an oxygen-containing gas in an inert organic solvent in the presence of a salcomine catalyst to produce a quinone and water, the improvement comprising carrying out said oxidation in the presence of a water-removing substance selected from the group consisting of carbodiimides, acetals, ketals, ortho-formates, vinyl ethers, and Type 3A and 4A molecular sieves.

2. A method of claim 1 wherein said water-removing substance is added to a solution of said phenol containing said catalyst.

3. A method of claim 1 wherein said phenol is dissolved in at least one inert organic solvent selected from the group consisting of acetonitrile, benzonitrile, methanol, dimethylformamide, N-methylpyrrolidone, benzene, and toluene.

4. A method of claim 1 wherein an aryl phenol is oxidized chiefly to a p-benzoquinone.

5. In a method of oxidizing a substituted phenol having a free para position with an oxygen-containing gas in an inert organic solvent in the presence of a salcomine catalyst to produce a quinone and water, the improvement comprising carrying out said oxidation in the presence of at least one water scavenger selected from the group consisting of carbodiimides, acetals, ketals, ortho-formates, and vinyl ethers.

6. A method of claim 5 wherein said water scavenger is dicyclohexylcarbodiimide.

7. A method of oxidizing an alkyl or aryl phenol having a free para position to a quinone comprising contacting the phenol with an oxygen-containing gas in an inert organic solvent in the presence of a salcomine catalyst and a water-removing substance selected from the group consisting of carbodiimides, acetals, ketals, ortho-formates, vinyl ethers, and Type 3A and 4A molecular sieves.

8. A method of claim 7 wherein said phenol is o-phenylphenol and said quinone is phenyl-p-benzoquinone.

9. A method of claim 7 wherein said phenol is contacted with said oxygen-containing gas at a temperature in the range of about from 25° C. to 100° C. and at an oxygen partial pressure in the range of about from 100 to 8000 kilopascals.

10. A method of claim 7 wherein said oxidation is carried out in the presence of dicyclohexylcarbodiimide.

* * * * *